United States Patent [19]

Tabak et al.

[11] 4,188,282
[45] Feb. 12, 1980

[54] MANUFACTURE OF BENZENE, TOLUENE AND XYLENE

[75] Inventors: Samuel A. Tabak, Wenonah; Roger A. Morrison, West Deptford, both of N.J.

[73] Assignee: Mobile Oil Corporation, New York, N.Y.

[21] Appl. No.: 914,645

[22] Filed: Jun. 12, 1978

[51] Int. Cl.$^2$ .......................... C10G 35/04; C07C 5/24
[52] U.S. Cl. ..................................... 208/134; 585/470; 585/481
[58] Field of Search ........................ 260/668 A, 672 T; 208/134

[56] References Cited

U.S. PATENT DOCUMENTS

| 3,856,871 | 12/1974 | Haag et al. | 260/668 A |
| 3,856,872 | 12/1974 | Morrison | 260/672 T |
| 3,856,873 | 12/1974 | Barress | 260/672 T |

Primary Examiner—C. Davis
Attorney, Agent, or Firm—Charles A. Huggett; Raymond W. Barclay

[57] ABSTRACT

Benzene, toluene and xylene are prepared from mixtures of single ring alkyl aromatic compounds of eight or more carbon atoms concurrently with isomerization of xylenes by mixing xylenes from which at least one isomer has been separated with a mixture of alkyl benzenes of eight and more carbon atoms, e.g. heavy reformate, and contacting that mixture at 800° to 1000° F. with a zeolite catalyst of reduced activity such as zeolite ZSM-5 having a silica to alumina ratio of at least 200.

34 Claims, 1 Drawing Figure

MANUFACTURE OF BENZENE, TOLUENE AND XYLENE

BACKGROUND OF THE INVENTION

Since the announcement of the first commercial installation of Octafining in Japan in June, 1958, this process has been widely installed for the supply of p-xylene. See "Advances in Petroleum Chemistry and Refining" volume 4 page 433 (Interscience Publishers, New York 1961). That demand for p-xylene has increased at remarkable rates, particularly because of the demand for terephthalic acid to be used in the manufacture of polyesters.

Typically, p-xylene is derived from mixtures of $C_8$ aromatics separated from such raw materials as petroleum naphthas, particularly reformates, usually be selective solvent extraction. The $C_8$ aromatics in such mixtures and their properties are:

|  | Freezing Point °F. | Boiling Point °F. | Density Lbs./U.S. Gal. |
|---|---|---|---|
| Ethylbenzene | −139.0 | 277.1 | 7.26 |
| P-xylene | 55.9 | 281.0 | 7.21 |
| M-xylene | −54.2 | 282.4 | 7.23 |
| O-xylene | −13.3 | 292.0 | 7.37 |

Principal sources are catalytically reformed naphthas and pyrolysis distillates. The $C_8$ aromatic fractions from these sources vary quite widely in composition but will usually be in the range 10 to 32 wt. % ethylbenzene with the balance, xylenes, being divided approximately 50 wt. % meta, and 25 wt. % each of para and ortho.

Individual isomer products may be separated from the naturally occurring mixtures by appropriate physical methods. Ethylbenzene may be separated by fractional distillation although this is a costly operation. Ortho xylene may be separated by fractional distillation and is so produced commercially. Para-xylene is separated from the mixed isomers by fractional crystallization.

As commercial use of para- and ortho-xylene has increased there has been interest in isomerizing the other $C_8$ aromatics toward an equilibrium mix and thus increasing yields of the desired xylenes. At present, several xylene isomerization processes are available and in commercial use.

The isomerization process operates in conjunction with the product xylene or xylenes separation processes. A virgin $C_8$ aromatics mixture is fed to such a processing combination in which the residual isomers emerging from the product separation steps are then charged to the isomerizer unit and the effluent isomerizate $C_8$ aromatics are recycled to the product separation steps. The composition of isomerizer feed is then a function of the virgin $C_8$ aromatic feed, the product separation unit performance, and the isomerizer performance.

It will be apparent that separation techniques for recovery of one or more xylene isomers will not have material effect on the ethylbenzene introduced with charge to the recovery isomerization "loop". That compound, normally present in eight carbon atom aromatic fractions, will accumulate in the loop unless excluded from the charge or converted by some reaction in the loop to products which are separable from xylenes by means tolerable in the loop. Ethylbenzene can be separated from the xylenes of boiling point near that of ethylbenzene by extremely expensive "superfractionation". This capital and operating expense cannot be tolerated in the loop where the high recycle rate would require an extremely large distillation unit for the purpose. It is a usual adjunct of low pressure, low temperature isomerization as a charge preparation facility in which ethylbenzene is separated from the virgin $C_8$ aromatic fraction before introduction to the loop.

Other isomerization processes operate at higher pressure and temperature, usually under hydrogen pressure in the presence of catalysts which convert ethylbenzene to products readily separated by relatively simple distillation in the loop, which distillation is needed in any event to separate by-products of xylene isomerization from the recycle stream. For example, the Octafining catalyst of platinum on a silicaalumina composite exhibits the dual functions of hydrogenation/dehydrogenation and isomerization.

In Octafining, ethylbenzene reacts through ethyl cyclohexane to dimethyl cyclohexanes which in turn equilibrate to xylenes. Competing reactions are disproportionation of ethylbenzene to benzene and diethylbenzene, hydrocracking of ethylbenzene to ethylene and benzene and hydrocracking of the alkyl cyclohexanes.

The rate of ethylbenzene approach to equilibrium concentration in a $C_8$ aromatic mixture is related to effective contact time. Hydrogen partial pressure has a very significant effect on ethyl benzene approach to equilibrium. Temperature change within the range of Octafining conditions (830° to 900° F.) has but a very small effect on ethylbenzene approach to equilibrium.

Concurrent loss of ethylbenzene to other molecular weight products relates to % approach to equilibrium. Products formed from ethylbenzene include $C_6+$ naphthenes, benzene from cracking, benzene and $C_{10}$ aromatics from disproportionation, and total loss to other than $C_8$ molecular weight. $C_5$ and lighter hydrocarbon by-products are also formed.

The three xylene isomerization reaction is much more selective than ethylbenzene conversion, but they do exhibit different rates of isomerization and hence, with different feed composition situations the rates of approach to equilibrium vary considerably.

Loss of xylenes to other molecular weight products varies with contact time. By-products include naphthenes, toluene, $C_9$ aromatics and $C_5$ and lighter hydrocracking products.

Ethylbenzene has been found responsible for a relatively rapid decline in catalyst activity and this effect is proportional to its concentration in a $C_8$ aromatic feed mixture. It has been possible then to relate catalyst stability (or loss in activity) to feed composition (ethylbenzene content and hydrogen recycle ratio) so that for any $C_8$ aromatic feed, desired xylene products can be made with a selected suitably long catalyst use cycle.

A different approach to conversion of ethylbenzene is described in Morrison U.S. Pat. No. 3,856,872, dated Dec. 24, 1974. Over an active acid catalyst typified by zeolite ZSM-5 ethylbenzene disproportionates to benzene and diethyl benzene which are readily separated from xylenes by the distillation equipment needed in the loop to remove by-products. It is recognized that rate of disproportionation of ethylbenzene is related to the rate of conversion of xylenes to other compounds, e.g. by disproportionation.

In the known processes for accepting ethylbenzene to the loop, conversion of that compound is constrained by the need to hold conversion of xylenes to an acceptable level. Thus, although the Morrison technique provides significant advantages over Octafining in this respect, operating conditions are still selected to balance the advantages of ethylbenzene conversion against the disadvantages of xylene loss by disproportionation and the like.

A further improvement in xylene isomerization, as described in application Ser. No. 818,171, filed July 22, 1977, utilizes a combination of catalyst and operating conditions which decouples ethylbenzene conversion from xylene loss in a xylene isomerization reaction, thus permitting feed of $C_8$ fractions which contain ethylbenzene without sacrifice of xylenes to conditions which will promote adequate conversion of ethylbenzene.

That improved process utilizes a low acid catalyst, typified by zeolite ZSM-5 of low alumina content ($SiO_2/Al_2O_3$ of about 500 to 3000 or greater) and which may contain metals such as platinum or nickel. In using this less active catalyst the temperature is raised to 800° F. or higher for xylene isomerization. At these temperatures, ethylbenzene reacts primarily via dealkylation to benzene and ethane rather than via disproportionation to benzene and diethylbenzene and hence is strongly decoupled from the catalyst acid function. Since ethylbenzene conversion is less dependent on the acid function, a lower acidity catalyst can be used to perform the relatively easy xylene isomerization, and the amount of xylenes disproportionated is eliminated. The reduction of xylene losses is important because about 75% of the xylene stream is recycled in the loop resulting in an ultimate xylene loss of 6–10 wt. % by previous processes.

Since most of the ethylbenzene goes to benzene instead of benzene plus diethylbenzenes, the product quality of the improved process is better than that of prior practices.

The improved process also allows greater flexibility with respect to charge stock. Since ethylbenzene conversion is relatively independent of isomerization, high ethylbenzene containing charge stocks can be processed, which means that charge stocks from thermal crackers (about 30 wt. % ethylbenzene) can be used as well as conventional stocks from reformers. In addition, dealkylation of $C_2+$ alkyl groups is favored since the temperature is above 800° F. As a result, paraffins in the charge stock will not alkylate the aromatic rings eliminating xylene loss via this mechanism. Thus, the improved process can process paraffins in the charge by cracking them to lighter paraffins eliminating the need for Udex Extraction. Finally, a small portion of the cracked fragments are recombined to form new aromatic rings which results in a net increase of aromatic rings.

The major raw material for p-xylene manufacture is catalytic reformate prepared by mixing vapor of a petroleum naphtha with hydrogen and contacting the mixture with a strong hydrogenation/dehydrogenation catalyst such as platinum on a moderately acidic support such as halogen treated alumina at temperatures favoring dehydrogenation of naphthenes to aromatics, e.g. upwards of 850° F. A primary reaction is dehydrogenation of naphthenes (saturated ring compounds such as cyclohexane and alkyl substituted cyclohexanes) to the corresponding aromatic compounds. Further reactions include isomerization of substituted cyclopentanes to cyclohexanes, which are then dehydrogenated to aromatics, and dehydrocyclization of aliphatics to aromatics. Further concentration of aromatics is achieved, in very severe reforming, by hydrocracking of aliphatics to lower boiling compounds easily removed by distillation. The relative severity of reforming is conveniently measured by octane number of the reformed naphthas, a property roughly proportional to the extent of concentration of aromatics in the naphtha (by conversion of other compounds or cracking of other compounds to products lighter than naphtha).

The conventional techniques make BTX available from the "gasoline pool" of the petroleum fuels industry. This is an unfortunate result, particularly under present trends for improvement of the atmosphere by steps to reduce hydrocarbon and lead emissions from internal combustion engines used to power automotive equipment.

By far the greatest amount of unburned hydrocarbon emissions from cars occurs during cold starts while the engine is operating below design temperature. It has been contended that a more volatile motor fuel will reduce such emissions during the warm-up period. In addition, the statutory requirements for reduction and ultimate discontinuance of alkyl lead anti-knock agents require that octane number specifications be met by higher content of high octane number hydrocarbons in the motor fuel.

The net effect of the trends in motor fuel composition for environmental purposes is increased need for light aromatics to provide high volatility and octane number for motor gasoline. Present practices for supply of BTX to the chemical industry run counter to the needs of motor fuel supply by removing the needed light aromatics from availability for gasoline blending.

It is known that acid zeolites are very effective for disproportionation of alkyl aromatic compounds. See Frilette et al. U.S. Pat. No. 3,506,731, Wallace et al. U.S. Pat. No. 3,808,284 and Inoue et al. U.S. Pat. No. 3,671,602. The latter has shown that heavier aromatics, e.g. tri-methyl benzenes may be disproportionated to BTX and $C_{10}+$ aromatics. The problem with that course is that a substantial portion of the product is $C_{10}+$ aromatics which boil $>350°$ F., which is at the upper limit or above the gasoline range and has little or no value as chemicals.

Typical processes for solving this problem by generation of BTX from heavy reformate, primarily by cracking off side chains of two or more carbon atoms, are described in U.S. Pat. Nos. 3,945,913, 3,948,758 and 3,957,621.

In a typical operation according to U.S. Pat. No. 3,945,913, heavy reformate is introduced to the xylene recovery/isomerization loop to blend with the stream of xylenes poor in P-xylene from the separation step. The conditions in the isomerization reactor are conducive to disproportionation. That feature makes it desirable to recycle the $C_9+$ fractions to generate additional xylenes by conversion of, e.g. trimethyl benzene. See FIG. 2. The process of U.S. Pat. No. 3,957,621 also involves addition of a heavy reformate to the loop, the patent noting the greater stability at high temperature of zeolite ZSM-5 having a high silica to alumina ratio. Here again, the $C_9$ aromatics are recycled to the reactor.

SUMMARY OF THE INVENTION

We have now found that the conditions for our process of xylene isomerization described in our said application Ser. No. 818,171 are very well suited to practice of converting heavy reformate to BTX. So well suited are those conditions that the present invention contemplates adding heavy reformate or other mixture of alkyl benzenes having eight and/or more carbon atoms to the charge for our improved xylene isomerization process as set forth in the said application Ser. No. 818,171. Due to the high conversion of ethylbenzene which can be achieved by our improved isomerization process, the quantity of material flowing in the loop (loop traffic) can be substantially reduced while maintaining the same level of xylenes in the loop. The capacity thus made available is advantageously filled by adding an equivalent amount of heavy reformate. Thus a plant designed for practice of Octafining or for practice of the process of said U.S. Pat. No. 3,856,872 may be converted to maintain the same flow of xylenes in the loop and the same level of feed of $C_8$ compounds for production of a desired xylene isomer (usually p-xylene) and concurrently convert a substantial quantity of heavy reformate to BTX. Therefor, an important object of the invention contemplates upgrading of existing plants for isomerization of xylene by replacing the catalyst with a crystalline aluminosilicate zeolite having a constraint index of 1 to 12, which zeolite is of substantially reduced activity. Preferably, the zeolite is associated with a metal having hydrogenation/dehydrogenation activity, such as a metal from Group VIII of the Periodic Table, preferably a noble metal such as platinum or palladium. The temperature is maintained in in the range of 800° F. to 1000° F. and heavy reformate is charged to the system between separation of p-xylene and isomerization.

Reduced activity of the zeolite for the present purpose may be attained by high silica/alumina ratio (above about 200), by dilution with a high preponderance of inert matrix, severe steaming, partial coking and other techniques known in the art.

BRIEF DESCRIPTION OF THE DRAWING

Apparatus for practice of a preferred embodiment of the invention is shown schematically in the single FIGURE of the drawing.

DESCRIPTION OF SPECIFIC EMBODIMENTS

Figure 1:
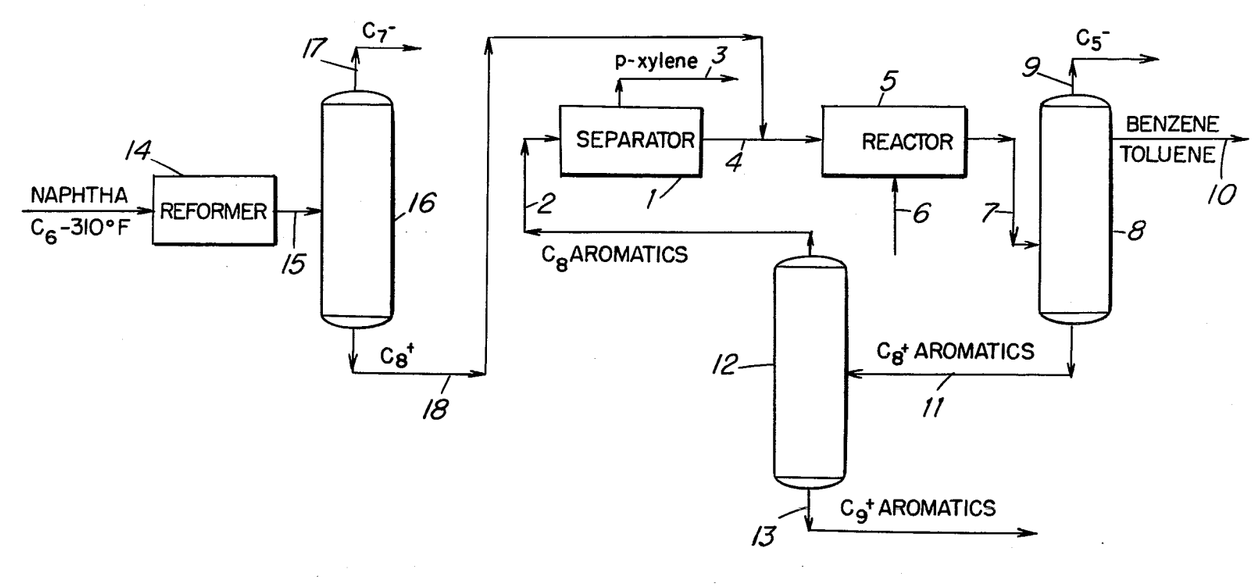

The foregoing objects and advantages of the invention are realized in that preferred embodiment thereof adapted to practice in a plant conforming to the flow sheet shown in the attached drawing. The plant includes the conventional isomerization/recovery loop in which a separator 1 removes, e.g., p-xylene from a mixture of $C_8$ aromatic compounds supplied thereto by line 2. Separator 1 may be of any of the types known for separation of a single xylene isomer. According to the embodiment illustrated, the product is p-xylene which can be recovered by fractional crystallization, selective sorption or the like as well known in the art, and discharged by line 3.

The residue of $C_8$ aromatics is transferred by line 4 to reactor 5 as a mixture lean in the isomer desired as principal product, p-xylene in this case. In reactor 5, that mixture is contacted with an isomerization catalyst under substantial pressure of hydrogen supplied by line 6. That catalytic reaction proceeds in a direction to restore the thermodynamic equilibrium of the xylene isomers, in the illustrated example by conversion of o-xylene and m-xylene to p-xylene. Isomerization effluent from reactor 5 contains the three isomers of xylene, ethylbenzene (EB) in amounts depending on EB content of raw feed to the loop and efficiency of the catalyst for conversion of EB. In addition, that effluent will contain by-products including paraffins, benzene, toluene and alkyl aromatics of nine or more carbon atoms. That effluent is fractionally distilled to separate the $C_8$ fraction for recycle to separator 1. Nature of the distillation train will depend on what products are desired. For example, o-xylene can be taken off as product in the distillation train.

According to the embodiment illustrated, p-xylene is the single $C_8$ aromatic product. The reactor effluent is transferred by line 7 to fractionating column 8 from which compounds of five or less carbon atoms are taken overhead at line 9 for use as fuel or other suitable purpose. A sidestream of benzene and toluene is taken at line 10 as a by-product valuable as chemical raw material.

The bottoms of column 8, constituted by alkyl aromatic compounds of eight or more carbon atoms are transferred by line 11 to fractionating column 12 from which compounds of nine or more carbon atoms are withdrawn as bottoms at line 13. Overhead of column 12 constitutes the feed by line 2 to separator 1. In the conventional operation, recycle feed in line 2 is admixed with fresh feed of $C_8$ aromatics prepared by distillation of an aromatic-rich fraction such as that derived by platinum reforming of a petroleum naphtha. That distillation is conducted to separate the hydrocarbons of eight carbons, both aromatic and paraffinic. The resultant $C_8$ fraction is treated with a selective solvent to separate paraffins from aromatics, providing a feed stock to the loop consisting essentially of the four $C_8$ aromatic compounds, namely ethylbenzene and the three xylenes. It will be seen that the separator is loaded by ethylbenzene of the charge in addition to that remaining in the recycle stream, a condition which is tolerated to avoid the loss of xylenes if fresh feed were delivered to the isomerizer to remove some part of the ethylbenzene content.

Because the reactor of the present invention provides a net increase in xylenes over the amount in the charge and because it is very effective for conversion of ethylbenzene, it is preferable that fresh charge be introduced to the loop between the separator and the reactor by admixing the same with the effluent of separator 1, lean in p-xylene. The reactor operation according to this invention has capability for conversion of paraffins in the charge, largely to $C_3$ and $C_4$ paraffins valuable as liquefied petroleum gas (LPG) as contrasted with methane and ethane of lower value for use as boiler fuel and requiring greater amounts of costly hydrogen for formation. Accordingly, the solvent separation of paraffins is not required and a fraction of reformate prepared only by distillation is the preferred feed.

An additional feature of the present invention is that side chains of two or more carbon atoms are removed from the benzene rings at the high temperature employed, converting ethylbenzene to benzene, methylethylbenzene to toluene, dimethylethylbenzene to xylene and the like. The resultant methyl benzenes do not equilibrate by transalkylation. Thus triethyl benzenes, whether present in the reformate or formed by splitting off an ethyl group will remain in the products of reaction. The invention therefore contemplates charge to the loop between separator 1 and reactor 5 of a mixture containing all the alkyl benzenes of eight or more carbon atoms present in the raw feed, such as reformate.

These departures from conventional commercial practice are illustrated in the drawing. Light virgin naphtha is separated from crude petroleum to include six carbon atom hydrocarbons and heavier material up to a suitable cut point, say 310° F. That naphtha is introduced to a reformer 14 wherein naphthenes are dehydrogenated to aromatic hydrocarbons. Reformer effluent is transferred by line 15 to a fractionating column 16 from which light reformate constituted by seven carbon atom hydrocarbons and lighter are taken overhead by line 17 for processing to provide gasoline blending stock of high octane number and high volatility. Since benzene and toluene free of paraffins are generated in the process, chemical needs for these compounds can be satisfied without depriving gasoline of these premium components. Bottoms of column 16 pass by line 18 to transfer line 4 for blending with the effluent of separator 1 for introduction to reactor 5.

A further advantage accrues to the present invention by elimination of the $C_8/C_9$ splitter used according to prior practices of recovering BTX from naphthas. That distillation normally leaves some $C_8$ aromatics in the heavier cut. These are now preserved for recovery by the present process.

The reactor 5 contains a crystalline aluminosilicate (zeolite) catalyst of relatively low acid activity. That catalyst, which is preferably combined with a metal for Group VIII of the Periodic Table promotes a reaction course which is unique at temperatures upwards of 800° F. Ethylbenzene in the charge is selectively cracked to benzene and ethane at little or no conversion of xylenes. Two or more carbon atom chains on other aromatics undergo like conversion. The two types of conversion are decoupled such that, for the first time, reaction severity is not a compromise to achieve effective ethyl aromatic conversion at "acceptable" loss of xylene. This characteristic of the process renders unnecessary the preliminary distillation to separate at least some of the ethyl benzene and $C_9+$ aromatics from the feed stream as practiced in prior processes. It has been further found that the present process has capability to convert paraffin hydrocarbons. This makes it possible to dispense with the expensive extraction step conventionally applied to a fraction of catalytically reformed naphthas in the manufacture and recovery of xylenes. In taking advantage of this feature, the feed stream at line 18 will contain the $C_8+$ aromatics of a reformate or the like together with the paraffins of like boiling range, nonanes and heavier. The paraffins in the charge are hydrocracked to lighter paraffins which will come off column 8 in much greater quantity than that resulting from conversion of ethylbenzene.

The ability of the process to handle heavy aromatics presents the possibility of charging to the reformer a wider cut than the 310° F. end point naphtha discussed in the above example, resulting in heavier aromatics in charge to the reactor of this process. Those heavy aromatics will be converted to provide additional benzene and toluene plus additional trimethyl benzene valuable as motor fuel.

Particularly preferred catalysts for reactor 5 are those zeolites having a constraint index within the approximate range of 1 to 12. Zeolites characterized by such constraint indices induce profound transformations of aliphatic hydrocarbons to aromatic hydrocarbons in commercially desirable yields and are generally highly effective in conversion reactions involving aromatic hydrocarbons. These zeolites retain a degree of crystallinity for long periods in spite of the presence of steam at high temperature which induces irreversible collapse of the framework of other zeolites, e.g. of the X and A type. Furthermore, carbonaceous deposits when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination, a silica to alumina mole ratio of at least about 12; and a structure providing constrained access to the crystalline free space.

In a preferred embodiment, the desired low activity is achieved by unusually high silica/alumina ratio, greater than 200, preferably above 500.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Such zeolites, after activation, acquire an introcrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methyl pentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
| --- | --- |
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperatures employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with probability, in some instances, of compounding variables extremes.

While the above experimental procedure will enable one to achieve the desired overall conversion of 10 to 60% for most catalyst samples and represents preferred conditions, it may occasionally be necessary to use somewhat more severe conditions for samples of very low activity, such as those having a very high silica to alumina ratio. In those instances, a temperature of up to about 1000° F. and a liquid hourly space velocity of less than one, such as 0.1 or less, can be employed in order to achieve a minimum total conversion of about 10%.

The class of zeolites defined herein is exemplified by ZSM-5, ZSM-11, ZSM-12, ZSM-35, ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-35 is more particularly described in U.S. Pat. No. 4,016,245, the entire contents of which are incorporated herein by reference.

ZSM-38 is more particularly described in U.S. Pat. No. 4,046,859, the entire contents of which are incorporated herein by reference.

A particularly preferred form of zeolite ZSM-5 is formed by crystallization of the zeolite from a solution containing metal ions, such as platinum as described in application Ser. No. 813,406 filed July 5, 1977 and now abandoned, the entire contents of which are incorporated herein by reference.

The best results so far have been obtained with such ZSM-5 variants prepared by co-crystallization of metal and zeolite which are conveniently given the designation ZSM-5- (cc M), where M stands for the metal co-crystallized (cc) with the zeolite during synthesis. ZSM-5-(cc Pt) with 0.2–0.8 wt % Pt has proved particularly effective in the present process.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite: however, the presence of these cations does appear to favor the formation of this special type of zeolite. More generally it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicate are ZSM-5, ZSM-11, ZSM-12, ZSM-35, and ZSM-38, with ZSM-5 or its metal containing variant particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired. Therefore, the preferred zeolites of this invention are those having a constraint index as defined above of about 1 to about 12, a silica to aluminum ratio of at least about 500 and a dried crystal density of not less than about 1.6 grams per cubic centimeter. The dry density for known structures may be calculated from the number of silicon plus aluminum atoms per 1000 cubic Angstroms, as given, e.g. on page 19 of the article on Zeolite Structure by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pykometer techniques. For example, it may be determined by immersing the dry hydrogen form of the zeolite in an organic solvent which is not sorbed by the crystal. It is possible that the unusal sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clays, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such an alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The invention utilizes zeolites of the type described, limited however to those forms which are of relatively low acid activity. It has been found that, as activity of these zeolites is reduced, the capacity to catalyze disproportionation declines without substantial decline in the capacity to catalyze isomerization of xylenes at temperatures above about 800° F. The invention takes advantage of that unique characteristic to achieve the processing advantage that isomerization is decoupled from ethylbenzene conversion which now proceeds by dealkylation in the presence of the low activity zeolite and the metal component. A significant consequence of these catalytic properties is that recycle of toluene and trimethylbenzene to the reactor is generally undesirable. The lack of disproportionation activity means that these methylbenzenes will not be converted in significant amounts to xylenes. Hence recycle of these unreactive species results in undesirable build-up in the loop of diluent materials.

The low acid activity of the catalyst is attainable in any of several ways or a combination of these. A preferred alternative is to form the zeolite at high silica/alumina ratio above 200, preferably above 500. Very high dilution with an inert matrix is also effective. For example, composites of a more active form of zeolite ZSM-5 with alumina at a ratio of 5 parts of zeolite with 95 parts of the inert matrix provides a suitable catalyst as described in our application Ser. No. 795,046, filed May 9, 1977 and now abandoned, the entire contents of which are incorporated herein by reference.

Activity of these zeolites may be reduced to levels suited to practice of the invention by thermal treatment or steam at high temperature as described in application Ser. No. 582,025, filed May 22, 1975, now U.S. Pat. No. 4,016,218, and in U.S. Pat. No. 3,965,209, respectively. Zeolites employed in such severe reactions as aromatization of paraffins and olefins lose activity to an extent which makes them suitable for use in the process of this invention. See U.S. Pat. No. 3,960,978 for fuller discussion of this manner of deactivated zeolite. Another method for reducing activity is to provide basic cations such as sodium at a significant proportion of the cationic sites of the zeolite. That technique is described in U.S. Pat. No. 3,899,544.

By whatever means the reduced acid activity is achieved, the activity may be measured in terms of disproportionation activity. A suitable test for the purpose involves contacting xylenes in any convenient mixture or as a single pure isomer over the catalyst at 900° F., 200 psig and liquid hourly space velocity (LHSV) of 5. Suitable catalysts for use in the process of the invention will show a single pass loss of xylenes (by disproportionation) of less than 2 weight percent, preferably less than one percent. Catalysts which have been employed show losses in the neighborhood of 0.5 percent. It is this very low rate of disproportionation at very high levels of ethylbenzene conversion to benzene (about 30%) that provides the advantage of the new chemistry of aromatics processing characteristic of the invention. That lack of disproportionation (and transalkylation generally) activity also dictates withdrawal of compounds boiling above and below eight carbon atom aromatic compounds. For example, toluene and trimethyl benzene are converted to very little, if any, extent and become diluents which occupy reactor space to no advantage. Small amounts of such diluents can be tolerated, such as those present by reason of "sloppy" fractionation, but withdrawal to at least a major extent is important to efficient operation.

EXAMPLES 1-4

Nature of conversion of various components of the heavy end of reformate according to this invention are shown in results of experimental runs charging the fraction of a commercial reformate cut by fractionation at 305° F. and having the composition shown below:

| Composition of 305 + °F. Reformate | |
|---|---|
| Ethylbenzene (EB) | 0.9 wt. % |
| xylenes | 7.4 |
| $C_9$ + Paraffins | 2.3 |
| $C_9$ Aromatics | 58.9 |
| $C_{10}$ Aromatics | 22.2 |
| $C_{11-12}$ Aromatics | 5.3 |
| $C_{13}$ + Aromatics | 3.0 |
| | 100.0 |

Conditions of reaction and analysis of yields are shown in Table 1 below. In each run the catalyst was a zeolite having essentially the X-ray diffraction pattern of ZSM-5 having the silica/alumina ratios and metals shown in Table 1. The space velocities are by weight (WHSV) with respect to total catalyst. The catalyst in each of Examples 1, 2 and 3 consisted of 65 wt. % of the specified zeolite plus metal and 35% alumina binder. The catalyst of Example 4 had no binder, but consisted of the stated zeolite and metal. Selectivities stated are % yield of $C_8^-$ aromatics divided by % conversion of $C_9$+ charge, multiplied by 100.

Table 1

| Example | 1 | 2 | 3 | 4 |
|---|---|---|---|---|
| Catalyst | | | | |
| Silica/alumina | 1600 | 1600 | 1600 | 660 |
| Metal (wt. %) | Pt(0.1) | Pt(0.1) | Ni(4.0) | Pt(0.23) |
| Temperature, °F. | 900 | 900 | 900 | 900 |
| Pressure, psig | 200 | 200 | 200 | 200 |
| WHSV | 10 | 5 | 20 | 20 |
| $H_2$/hydrocarbon, molar | 5 | 5 | 5 | 5 |
| Material Balance | 100.9 | 98.8 | 100.0 | 100.2 |
| Products | | | | |
| $C_1$-$C_6$ Paraffins | 9.78 | 12.45 | 6.55 | 5.09 |
| Benzene | 3.62 | 4.25 | 2.93 | 3.40 |
| $C_7$ Paraffins | 0.05 | 0.06 | 0.05 | 0.02 |
| Toluene | 14.98 | 17.42 | 9.38 | 7.98 |
| $C_8$ Paraffins | 0.03 | 0.02 | 0.03 | 0.02 |
| Ethylbenzene | 1.75 | 1.15 | 1.83 | 1.22 |

Table 1-continued

| Example | 1 | 2 | 3 | 4 |
|---|---|---|---|---|
| m-Xylene | 7.36 | 7.98 | 6.04 | 5.15 |
| p-Xylene | 3.32 | 3.59 | 2.70 | 2.26 |
| o-Xylene | 3.19 | 3.47 | 2.61 | 3.35 |
| $C_9$+ Paraffins | — | 0.08 | 0.22 | 0.18 |
| $C_9$ Aromatics | 37.30 | 28.24 | 42.69 | 43.53 |
| $C_{10}$ Aromatics | 11.17 | 14.72 | 20.12 | 23.77 |
| $C_{11-12}$ Aromatics | 6.43 | 5.55 | 4.17 | 3.20 |
| $C_{13}$+ | 1.08 | 1.06 | 0.67 | 0.79 |
| % Conversion $C_9$+ | 35.72 | 42.13 | 24.04 | 20.40 |
| EB made | 0.85 | 0.25 | 0.93 | 0.32 |
| Xylenes made | 6.47 | 7.64 | 3.95 | 3.36 |
| Toluene made | 14.92 | 17.42 | 9.38 | 7.98 |
| Benzene made | 3.62 | 4.25 | 2.93 | 3.40 |
| Selectivity | 73 | 70 | 72 | 74 |

According to one preferred embodiment of the invention, the catalyst is the variant of zeolite ZSM-5 having a high silica/alumina ratio and containing a transition metal in unique form by reason of a salt of the metal in the crystallization medium at the time the crystals were formed. Preparation of two such catalysts containing co-crystallized platinum are briefly described in Examples 5 and 6.

EXAMPLE 5

Zeolite ZSM-5 having a silica to alumina ratio of 660 and containing 0.23% by weight of co-crystallized platinum was prepared for use in accordance with this invention.

The following reactants were heated together:

| Water | 710 grams |
|---|---|
| Chloroplatinic acid (40 wt. % Pt) | 3 |
| Hydrochloric acid | 35 |
| Tetraethyl Ammonium Bromide | 25 |
| Water Glass | 290 |
| 8.9% $Na_2O$ | |
| 28.7% $SiO_2$ | |
| 62.4% $H_2O$ | |
| 0.046% $Al_2O_3$ | |

The product contained 0.23% platinum in ZSM-41 of 660 silica/alumina.

EXAMPLE 6

Zeolite ZSM-5 having a silica to alumina ratio of 1041 and containing 0.76% by weight of co-crystallized platinum was prepared for use in accordance with the invention.

The following reactants were heated together:

| Water | 600 grams |
|---|---|
| Tetrapropylammonium bromide | 100 |
| Chloroplatinic acid (40 wt. % Pt) | 3 |
| $Al_2(SO_4)_3$ . 14 $H_2O$ | 0.77 |
| Tetraethyl orthosilicate | 314 |
| 50% NaOH solution | 21.2 |

After crystallization was complete, the crystals were separated by filtration, washed with water, dried, base exchanged with ammonium cation and calcined at about 1000° F.

Two comparative runs demonstrate an important advantage of adding heavy reformate to the high temperature isomerization of xylenes over low activity ZSM-5 described in the said copending application Ser. No. 818,171. The comparative runs are identified as Examples 7 and 8 in Table 2. The zeolite used in both examples was co-crystallized platinum ZSM-5 of about 1000 silica/alumina ratio and containing about 0.4 weight percent platinum. The catalyst pellets were a composite of 30 weight percent of that zeolite with 70 weight percent alumina.

TABLE 2

|  | Example 7 | | Example 8 | |
|---|---|---|---|---|
| Temp. (°F.) | | 870 | | 870 |
| Pressure (Psig) | | 200 | | 200 |
| WHSV | | 8 | | 8 |
| H$_2$/HC | | 5 | | 5 |
| Mat. Bal. | | 97.62 | | 98.86 |
| Hrs. on Stream | Charge | 2 | Charge | 37 |
| C$_1$–C$_6$'s | | 1.33 | | 3.02 |
| Benzene | | 4.17 | | 3.51 |
| C$_7$'s | | — | | — |
| Toluene | 0.1 | 0.53 | | 3.00 |
| C$_8$'s | | 0.01 | | .01 |
| EB | 14.7 | 8.88 | 11.1 | 7.49 |
| M-Xylene | 68.2 | 45.92 | 50.3 | 35.22 |
| P-Xylene | 9.4 | 19.94 | 8.9 | 15.25 |
| O-Xylene | 7.4 | 18.43 | 6.1 | 13.54 |
| C$_9$+ Par. | 0.2 | — | 0.7 | 0.13 |
| C$_9$ Ar | | 0.63 | 15.2 | 11.76 |
| C$_{10}$ Ar | | 0.06 | 8.4 | 5.56 |
| C$_{11-12}$ Ar | | 0.03 | 1.1 | 1.15 |
| C$_{13}$+ | | 0.06 | 0.2 | .23 |
| Wt % EB Conv. | | 39.59 | | 32.52 |
| Wt % C$_9$+ Conv. | | — | | 24.50 |
| Xylenes Made | | −.61 | | .71 |
| Wt % M-XYL | | 54.47 | | 55.03 |
| P-XYL } 100% | | 23.66 | | 23.82 |
| O-XYL | | 21.87 | | 21.15 |
| Net Gain over Ex. 7 | | | | |
| Benzene | | | | .85 |
| Toluene | | | | 2.47 |
| Xylene | | | | 1.32 |
| Total BTX Gain | | | | 4.64 |
| LB BTX/LB C$_9$+ Conv. | | | | .76 |
| LB BTX/LB C$_9$+ Chg. | | | | .18 |

Example 7 illustrates the capability of the catalytic system to effectively isomerize xylene at a xylene loss below 1% while converting ethyl benzene to the extent of about 40%. The benzene in the product is roughly equivalent to the amount of ethyl benzene converted, justifying the assumption that the only significant conversion of ethyl benzene is dealkylation. The very small loss of xylenes shows that disproportionation reactions are negligible, a conclusion further justified by the very low yield of aromatics of nine or more carbon atoms. This is to be contrasted with prior practices wherein conversion of ethyl benzene has been largely disproportionation to benzene and diethyl benzene. Note the trace of C$_{10}$ aromatics obtained in Example 7.

The charge in Example 7 is typical of the feed stream to the isomerizer in an operation to recover both p-xylene and o-xylene from the C$_8$ aromatics of reformate. The charge in Example 8 is a similar recycle stream blended with the heavy end of a commercial reformate boiling above 305° F. and corresponds to feed streams typical of those utilized in the invention. The nature of products obtained demonstrates the nature of the conversions taking place according to this invention. Aromatic side chains of two or more carbon atoms are split off. Thus ethyl benzene and propyl benzene are converted to benzene. Methylethylbenzene yields toluene. Trimethyl benzenes undergo no significant change. For the charge employed, the maximum theoretical conversion of C$_9$+ aromatics to C$_8$— under these conditions described is about 50%.

The advantages accruing in use of the present invention are forcefully brought out by consideration of a set of engineering estimates for adaptation of a plant designed for practice of the xylene isomerization process of the above-cited U.S. Pat. No. 3,856,872. Such plant charging 5000 barrels per day (BPD) of C$_8$ aromatics containing 17% EB (balance essentially xylenes) will have a loop traffic of 26,000 BPD measured at the point of maximum flow in the loop at 19.8% EB conversion and will yield products as follows:

p-Xylene—3806 BPD
Benzene—340
Toluene—154
C$_9$+ Aromatics—682

At the high temperature, high silica catalyst conditions of our above cited application Ser. No. 818,171, 35% EB conversion is appropriate with 0.5% xylene loss per pass by disproportionation and converted EB going 97% to benzene, 3% to C$_{10}$ aromatics. Still maintaining the charge rate of 5000 BPD C$_8$ aromatics, the loop traffic at high temperature, high silica catalyst is 21,000 BPD with products as follows:

p-Xylene—4038
Benzene—607
Toluene—49
C$_9$+ Aromatics—95

Not only has the high temperature operation provided an increased yield of the most valuable products p-xylene and benzene but it has also made available 5000 BPD of loop traffic which can be filled by charging the C$_9$+ fraction of reformate together with the C$_8$ fraction such that the charge is now the C$_8$+ fraction. At 35% total conversion, products from the C$_9$+ portion of the charge will be:

p-Xylene—319 BPD
Benzene—206
Toluene—741
C$_9$+ Aromatics—3251

Combining the yields from the two stated portions of charge (full loop traffic) and comparing against the first case (full loop traffic per U.S. Pat. No. 3,856,872), the following results are found:

|  | Total Products This Invention | Increase Over 3,856,872 Process |
|---|---|---|
| p-Xylene | 4357 BPD | 551 BPD |
| Benzene | 813 | 473 |
| Toluene | 790 | 636 |

These calculations are for single pass operation assuming recycle of ethylbenzene, o-xylene and m-xylene to extinction. If desired, a minor amount of C$_9$+ aromatics may also be recycled, backing out some of the virgin charge. It is preferred that C$_9$ and heavier hydrocarbons be withdrawn at this point, at least to a major extent. Since the process involves little, if any, disproportionation, trimethyl benzenes will tend to build up in the system. These heavier aromatics are preferably withdrawn for gasoline or other end use as desired. The invention therefor provides an attractive means for improvement of existing plant facilities, including those for practice of Octafining by replacement of catalyst and minor changes in piping and operating controls. In addition, the invention affords a saving in operating cost through elimination of the splitter column for separation of $C_8$ from higher boiling fractions and the preferred elimination of extraction to remove paraffins.

In summary, advantages of the invention are seen to include:

In single pass operation, the process dealkylates up to 90+% of the ethyl and propyl benzenes, resulting in higher yields of the more commercially valuable BTX from the $C_9+$ reformate charged. The quantity and composition of BTX produced depends on the composition of the $C_9+$ portion of reformate charged. However, yields of 0.25 lb BTX/lb $C_9+$ charged do not seem unreasonable for single pass operation. Following the single pass unconverted $C_9+$ can be returned to the gasoline pool.

In recycle operation it dealkylates ethylbenzene almost completely to benzene, rather than benzene and $C_{10}$ aromatics as in prior practices.

In recycle operation, it isomerizes xylenes, exhibiting a net increase (0.3–1.0%) of xylenes. This elimination of xylene loss is important because approximately 80% of the xylenes are recycled, which in the best of prior processes results in an ultimate 6–10% xylene loss.

The system can process paraffin charge without increasing xylene losses from alkylation, thus eliminating the need for paraffin extraction.

The weight hourly space velocity values given in the specific examples above are based on the total catalyst composite of active zeolite, metal and inert matrix, such as alumina. This is the convenient manner of expressing that value and is meaningful as applied to those catalysts in which the zeolite predominates. However, with regard to catalysts in which low activity is attained by very high dilution (as low as 1 weight percent zeolite or even less) the space velocity should be related to the weight of active zeolite and the term is so used in the appended claims. Thus a WHSV of 5 with respect to catalyst of 1% zeolite in 99% of alumina corresponds to WHSV of 500 with respect to total weight of the zeolite/alumina composite. On that basis, the invention contemplates space velocities of 1500 and higher based on weight of composite to provide highly diluted zeolite.

We claim:

1. A new use of known apparatus for simultaneously isomerizing xylenes and converting ethylbenzene to products readily separable by distillation from the mixture of $C_8$ aromatics by contacting a mixture of $C_8$ aromatics and hydrogen with a catalyst at conversion conditions of elevated temperature and pressure in a loop comprising an isomerization reactor for the contact aforesaid, distillation means for separating $C_8$ aromatics from lower boiling and higher boiling hydrocarbons, means to transfer hydrocarbon effluent of said isomerization reactor to said distillation means, mixing means for mixing fresh feed $C_8$ aromatics containing xylenes and ethylbenzene with $C_8$ aromatics separated by distillation means, a xylene separator for recovery of para xylene, means for transfer of mixed $C_8$ aromatics from said mixing means to said xylene separator, and means to transfer $C_8$ aromatics lean in para xylene from said xylene separator to said isomerization reactor, which new use comprises contacting, in the isomerization reactor of said known apparatus, a vapor phase mixture of hydrogen, said $C_8$ aromatics lean in para xylene and fresh charge material containing alkyl benzenes of more than eight carbon atoms with a zeolite catalyst at a temperature of about 800°–1000° F., a pressure of 150 to 300 pounds per square inch and a weight hourly space velocity between 1 and about 200; said zeolite catalyst having a constraint index of 1 to 12, a silica to alumina ratio greater than 12 and a reduced activity such that less than 2 weight percent of xylene is converted to other compounds when contacted with said catalyst at 900° F., 200 psig and LHSV of 5.

2. The new use defined by claim 1 wherein said zeolite is in the acid form.

3. The new use defined by claim 1, wherein said silica to alumina ratio is greater than 200.

4. The new use defined by claim 1, wherein said silica to alumina ratio is greater than 500.

5. The new use defined by claim 1 wherein a metal of Group VIII or a compound of such metal is associated with said zeolite.

6. The new use defined by claim 5 wherein said metal is co-crystallized with said zeolite.

7. The new use defined by claim 5 wherein said metal is platinum.

8. The new use defined by claim 1 wherein said zeolite is dispersed in a solid matrix.

9. In a process for isomerizing the xylene content of a charge mixture of eight carbon atom aromatic hydrocarbon compounds which mixture contains xylene, and ethylbenzene by contact at conversion conditions with a catalyst comprising a zeolite having a silica/alumina ratio greater than 12 and a constraint index of 1 to 12, the improvement resulting in conversion of ethylbenzene to benzene and conversion of higher alkyl benzenes to benzene, toluene and xylene which comprises including in the charge mixture alkyl aromatics of more than eight carbon atoms, maintaining the conversion temperature at about 800° F. to 1000° F. and using such catalyst comprising a zeolite of reduced acid activity such that less than 2 weight percent of xylene is converted to compounds other than xylene when contacted with said catalyst at 900° F. 200 psig and LHSV of 5.

10. A process according to claim 9 wherein said zeolite is in the acid form.

11. A process according to claim 9 wherein said zeolite is ZSM-5.

12. A process according to claim 9 wherein said catalyst also comprises a metal of Group VIII of the Periodic Table.

13. A process according to claim 12 wherein said zeolite is ZSM-5.

14. A process according to claim 12 wherein said charge mixture is admixed with hydrogen.

15. A process according to claim 14 wherein said zeolite is ZSM-5.

16. A process according to claim 9 resulting in conversion of ethylbenzene to benzene at substantially no loss of xylene in the product as compared to the charge.

17. A process according to claim 9 wherein the said charge mixture contains paraffin hydrocarbons.

18. A process according to claim 9 wherein the said charge mixture consists essentially of aromatic hydrocarbons.

19. A process according to claim 9 wherein said silica/alumina ratio is greater than 200.

20. A process according to claim 9, wherein said silica/alumina ratio is greater than 500.

21. A process for the manufacture of aromatic hydrocarbons which comprises subjecting a hydrocarbon naphtha to catalytic reforming under conditions to convert naphthenes to aromatic hydrocarbons in a reformate reaction product, distilling said reformate to separate compounds of less than eight carbons from a heavy reformate, mixing said heavy reformate with a recycle stream hereafter defined, contacting the resultant mixture at 800°–1000° F. with a zeolite catalyst having a constraint index of 1 to 12, a silica/alumina ratio above about 12 and reduced acid activity such that less than 2 weight percent of xylene is converted to compounds other than xylene when contacted with said catalyst at 900° F., 200 psig and LHSV of 5, whereby to isomerize xylene content of said mixture and to convert ethylbenzene and alkylbenzenes of more than eight carbon atoms to benzene, toluene and xylene, distilling the product of said contacting to separate compounds of less than eight carbon atoms and compounds of more than eight carbon atoms from a $C_8$ fraction, recovering at least one xylene isomer from said $C_8$ fraction to provide a stream lean in said recovered isomer and mixing said lean stream with said heavy reformate as the recycle stream aforesaid.

22. A process according to claim 21 wherein said zeolite is ZSM-5.

23. A process according to claim 21 wherein said zeolite is in the acid form.

24. A process according to claim 21 wherein said contacting is conducted under hydrogen pressure.

25. A process according to claim 21 wherein said zeolite is associated with a metal of Group VIII.

26. A process according to claim 25 wherein said metal is a noble metal of Group VIII.

27. A process according to claim 21 wherein said heavy reformate is treated with a solvent to separate paraffins therefrom.

28. A process according to claim 21 wherein said heavy reformate contains paraffin hydrocarbons.

29. A process according to claim 21 wherein said silica/alumina ratio is greater than 200.

30. A process according to claim 29 wherein said silica/alumina ratio is greater than 500.

31. A process according to claim 25 wherein said metal is co-crystallized with said zeolite.

32. A process according to claim 1 wherein the said zeolite catalyst has been steamed at high temperature to reduce activity thereof to the level aforesaid.

33. A process according to claim 9 wherein the said zeolite has been steamed at high temperature to reduce activity thereof to the level aforesaid.

34. A process according to claim 21 wherein the said zeolite catalyst has been steamed at high temperature to reduce activity thereof to the level aforesaid.

* * * * *

UNITED STATES PATENT AND TRADEMARK OFFICE
CERTIFICATE OF CORRECTION

PATENT NO. : 4,188,282
DATED : February 12, 1980
INVENTOR(S) : Samuel A. Tabak and Roger A. Morrison It is certified that error appears in the above-identified patent and that said Letters Patent are hereby corrected as shown below:

Col. 1, line 17: "be" should read -- by --.

Col. 7, line 31: "for" should read -- from --.

Col. 10, lines 66 & 67: "aluminum" should read -- alumina --.

Col. 13, line 34: "xylenes" should read -- Xylenes --.

Col. 13, line 51: "$C_8-$" should read -- $C_8^-$ --.

Col. 12, line 49: after "1977" Patent Office inserted -- and now abandoned --.

Col. 12, lines 55 & 56: after "1975" Patent Office inserted -- now U.S. Pat. No. 4,016,218 --.

Assignee: "Mobile" should read -- Mobil --.

References cited 3,856,873: "Barress" should read -- Burress --.

Signed and Sealed this

Fourth Day of November 1980

[SEAL]

Attest:

SIDNEY A. DIAMOND

Attesting Officer     Commissioner of Patents and Trademarks